US00PP10701P

United States Patent [19]

Spek

[11] Patent Number: Plant 10,701

[45] Date of Patent: Nov. 24, 1998

[54] POLYANTHA ROSE PLANT NAMED 'SPEVU'

[75] Inventor: Hette Spek, Boskoop, Netherlands

[73] Assignee: DeVor Nurseries, Inc., Watsonville, Calif.

[21] Appl. No.: 738,877

[22] Filed: Oct. 28, 1996

[51] Int. Cl.[6] ..... A01H 5/00

[52] U.S. Cl. ..... Plt./27

[58] Field of Search ..... Plt./22, 27, 28, Plt./29

[56] References Cited

PUBLICATIONS

UPOVROM, Plant Variety Database, 1997/03, GTI Jouve Retrieval Software, listings (7) for 'Spevu'.

*Primary Examiner*—Howard J. Locker
*Attorney, Agent, or Firm*—Christie, Parker & Hale, LLP

[57] ABSTRACT

A polyantha rose variety producing dark pink flowers.

1 Drawing Sheet

BACKGROUND OF THE INVENTION

The present invention relates to a new and distinct polyantha variety which was discovered by me as a sport in a controlled planting of the variety 'The Fairy' in Boskoop, Netherlands. The varietal denomination of this new rose is 'Spevu'.

SUMMARY OF THE INVENTION

Among the novel characteristics possessed by this new variety which distinguish it from its parent and all other varieties of which I am aware are its attractive dark pink flowers borne on a low growing plant.

Asexual reproduction by budding of the new variety as performed in Watsonville, Calif., shows that the foregoing and other distinguishing characteristics come true to form and are established and transmitted through succeeding propagations. Other known forms of asexual reproduction for roses may be also employed.

Comparison With Parent

The new variety produces dark pink flowers in contrast to light pink flowers of 'The Fairy'.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Sport of the variety 'The Fairy'.
Class: Polyantha.

The following is a detailed description of the new variety, from specimens grown outdoors in Watsonville, Calif., in the month of Sepember. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

Flower

Blooming habit: Continuous.

A. Bud:
- (1) *Size.*—Small, about 0.5 cm to 1 cm long, about 0.5 cm to 1 cm wide.
- (2) *Form.*—Cupped.
- (3) *Color.*—When sepals first divide, bud color is near 58B.
- (4) *Sepals.*—Slightly longer than bud, hairy on both sides; become horizontal when bloom opens, most are lanceolate but occasionally foliaceous with leaf-shaped ends. Color: Near 144A.
- (5) *Peduncle.*— *Length: About* 2 cm to about 3 cm. Aspect: Hairy with many prickles. Strength: Erect, slightly curved. Color: Near 144A with near 184C blush.
- (6) *Bracts.*—About 1 or 2.

B. Bloom:
- (1) *Size.*—Small, 3 to 3.5 cm.
- (2) *Borne.*—Sprays of about 11 to 42 blooms.
- (3) *Form.*—Cupped.
- (4) *Petalage.*—Number of petals under normal conditions— about 21 to 36.
- (5) *Color* (⅓–½ *open*).—Outer and inner petals — Top and bottom surface near 63A, lighten to near 63B when full open. Base of petals: Near 2A. General tonality from a distance: Dark pink.
- (6) *Color* (*Fully open*).—Outer petals — Top surface: top — near 61C; center — near 61C; base — near 155A; Under-surface; tip — near 67C; center — near 68A; base — near 155B. Inner petals — Top surface: near 61C; center — near 67C; base — near 155C; Undersurface: tip — near 67C; center — near 68A; base — near 155C. Base of petals: Near 4C. General tonality from a distance: Dark pink.
- (7) *Color change.*—Color lightens slightly. Petal top surface Lightens slightly to near 61D. Petal under-surface Changes to near 63B. General tonality at a distance Dark pink.

C. Petals:
- (1) *Texture.*—Thin.
- (2) *Appearance.*—Inside velvety and outside satiny.
- (3) *Form.*—Heart shaped.
- (4) *Arrangement.*—Imbricated.
- (5) *Petaloids.*—About 6 to 7.
- (6) *Fragrance.*—None.
- (7) *Lasting quality.*—On plant 14 to 18 days; about 10 to 12 days after cutting.

(8) *Persistence.*—Petals drop off cleanly.

Reproductive Organs

A. Stamens:
(1) *Arrangement.*—Irregularly arranged around styles.
(2) *Anthers.*—Color — near 167B.
(3) *Filaments.*—Color — near 150D.
(4) *Pollen.*—Color — near 156B.

B. Pistils:
(1) Styles.—Bunched, uneven.
(2) Stigmas.—Color — near 157A.

C. Characteristics of hips: Globose, about 0.05 cm, near 169C, seeds do not protrude.

Plant

A. Form: Compact, spreading.

B. Growth: Very vigorous; about, 37 cm to about 50 cm in height and about 35 cm in width at first season.

C. Foliage: Compound 3 to 7 leaflets.
(1) *Size.*—Medium, same size as 'The Fairy'.
(2) *Quantity.*—Abundant.
(3) *Color.*—New foliage — near 184D (both surfaces); mature foliage — upper side near 147A, Underside near 147B.
(4) *Shape.*—Acute.
(5) *Texture.*—Upper side leathery; semi glossy, smooth; underside leathery, matte.
(6) *Edge.*—Serrate.
(7) *Serration.*—Serrated.
(8) *Leaf stem.—Color — medium green.*
(9) *Stipules.*—Parallel, middle enlarged.
(10) *Rachis.*—Small prickles.
(11) *Petioles.*—Top near 146A, underside near 144A.
(12) *Auricle.*—Medium, pointed, curving slightly.
(13) *Resistance to disease.*—Very resistant to blackspot, mildew and rust.

D. Wood:
(1) *New wood.*—Color near 184D, bark smooth.
(2) *Old wood.*—Color near 137B, bark smooth.

E. Flower Stem: About 22 cm to about 30 cm from last cut.

F. Thorns:
(1) *Thorns.*—Quantity: On main stalk, few; laterals from stalk, few. Form: Wing-shaped. Length: Medium. Color: Near 184C. Position: Regular.
(2) *Prickles.*—Few.

G. Winter hardiness: Winter hardy in Watsonville, Calif.

I claim:

1. A new and distinct variety of polyantha rose plant substantially, as shown and described.

* * * * *

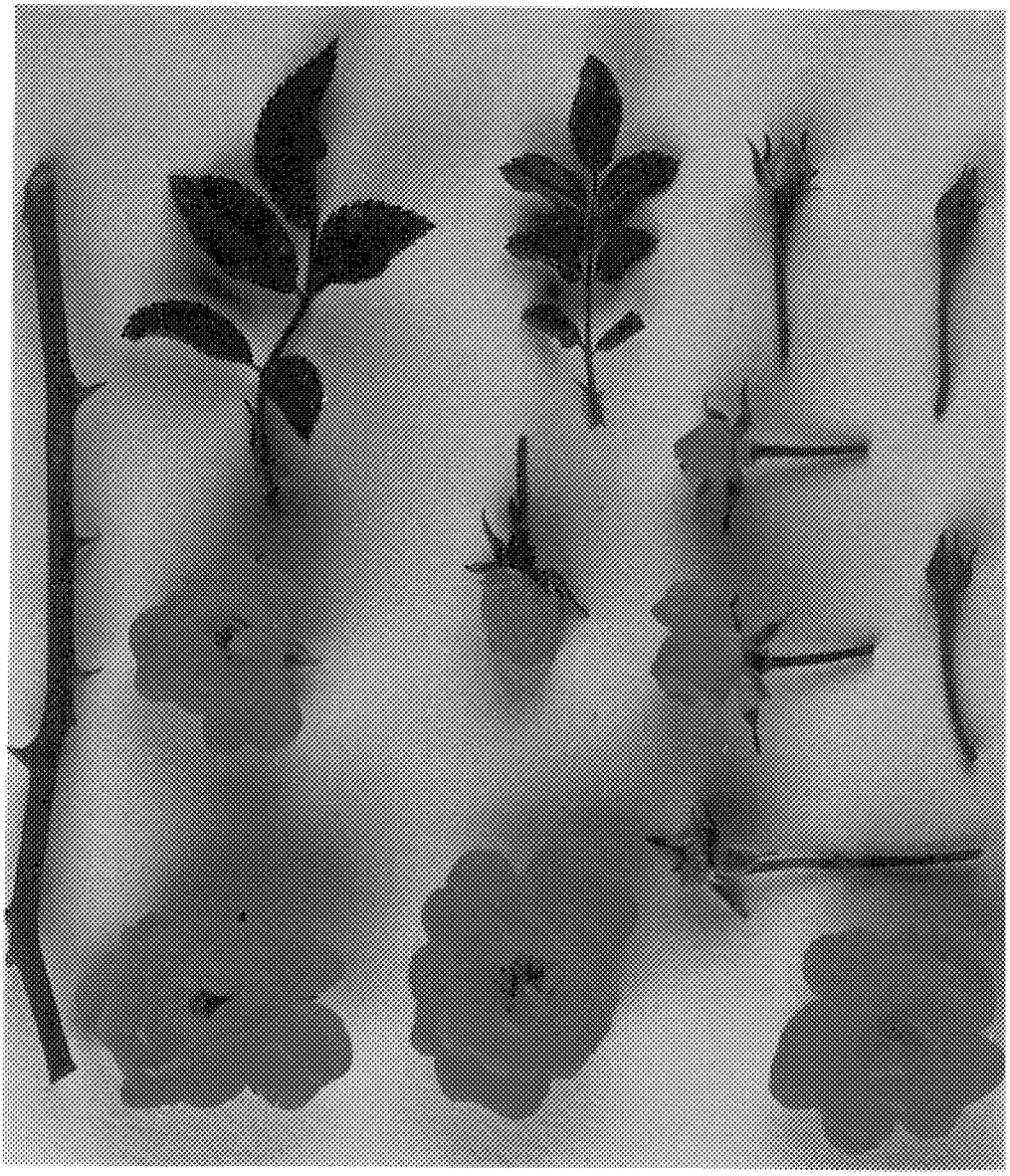

UNITED STATES PATENT AND TRADEMARK OFFICE

CERTIFICATE OF CORRECTION

PATENT NO. : Plant 10,701
DATED : November 24, 1998
INVENTOR(S) : Hette Spek

It is certified that error appears in the above-identified patent and that said Letters Patent is hereby corrected as shown below:

Column 2, line 29, replace "top — near 61C;" with -- tip — near 61C; --.

Signed and Sealed this
First Day of February, 2000

*Attest:*

Q. TODD DICKINSON

*Attesting Officer*

*Acting Commissioner of Patents and Trademarks*